(12) United States Patent
Jones

(10) Patent No.: US 8,772,356 B2
(45) Date of Patent: Jul. 8, 2014

(54) METHODS FOR TREATING AN INORGANIC SLURRY

(71) Applicant: Rhodia Operations, Aubervilliers (FR)

(72) Inventor: Christopher Raymond Jones, South Staffordshire (GB)

(73) Assignee: Rhodia Operations, Aubervilliers (FR)

( * ) Notice: Subject to any disclaimer, the term of this patent is extended or adjusted under 35 U.S.C. 154(b) by 0 days.

(21) Appl. No.: 13/856,058

(22) Filed: Apr. 3, 2013

(65) Prior Publication Data

US 2013/0225534 A1 Aug. 29, 2013

Related U.S. Application Data

(63) Continuation of application No. 13/586,012, filed on Aug. 15, 2012, now abandoned, and a continuation of application No. 10/542,432, filed as application No. PCT/GB2004/000056 on Jan. 12, 2004, now abandoned.

(30) Foreign Application Priority Data

Jan. 29, 2003 (GB) .................................. 0301975.9

(51) Int. Cl.
*B01F 3/12* (2006.01)
*C09C 1/02* (2006.01)

(52) U.S. Cl.
USPC .............................................. 516/1; 106/464

(58) Field of Classification Search
USPC ............................................................. 516/1
See application file for complete search history.

(56) References Cited

U.S. PATENT DOCUMENTS

| | | |
|---|---|---|
| 2,877,848 A | 3/1959 | Case |
| 3,336,221 A | 8/1967 | Raulston |
| 3,597,251 A | 8/1971 | Kaufman |
| 3,832,302 A | 8/1974 | Lansford et al. |
| 3,945,843 A | 3/1976 | Holty et al. |
| 4,673,509 A | 6/1987 | Davis et al. |
| 4,874,526 A | 10/1989 | Grade et al. |
| 5,386,038 A | 1/1995 | Davis et al. |
| 5,606,105 A | 2/1997 | Davis et al. |
| 5,741,757 A | 4/1998 | Cooper et al. |
| 6,180,056 B1 | 1/2001 | Comstock et al. |
| 6,315,867 B1 | 11/2001 | Skuse et al. |
| 6,402,824 B1 | 6/2002 | Freeman et al. |
| 2002/0144797 A1 | 10/2002 | Skuse et al. |
| 2003/0226808 A1 | 12/2003 | Fidoe et al. |

FOREIGN PATENT DOCUMENTS

| | | |
|---|---|---|
| EP | 0 491 391 A | 6/1992 |
| EP | 0 839 956 A | 5/1998 |
| EP | 1 160 201 A | 12/2001 |
| GB | 2 379 440 A | 3/2003 |
| WO | WO 96/14092 A1 | 5/1996 |
| WO | WO 99/33345 A | 7/1999 |
| WO | WO 00/04777 A | 2/2000 |
| WO | WO 02/08127 A | 1/2002 |

OTHER PUBLICATIONS

"slurry." Merriam-Webster Online Dictionary. 2009. Merriam-Webster Online. Jul. 2, 2009. <http://www.merriam-webster.com/dictionary/slurry>.

*Primary Examiner* — Peter F Godenschwager
(74) *Attorney, Agent, or Firm* — Holtz Holtz Goodman & Chick PC

(57) ABSTRACT

A method for treating an inorganic slurry to preserve the slurry against bacterial contamination, including (I) providing a slurry in a substantially homogeneous phase, and then (II) adding to the slurry an effective amount of a composition containing: (a) a tetrakis(hydroxyorgano)phosphonium salt selected from the group consisting of tetrakis(hydroxymethyl)phosphonium sulphate, tetrakis(hydroxymethyl)phosphonium chloride, tetrakis(hydroxymethyl)phosphonium phosphate, tetrakis(hydroxymethyl)phosphonium nitrate and tetrakis(hydroxymethyl)phosphonium oxalate; and (b) a dispersant selected from the group consisting of (i) a phosphonated compound containing at least one tertiary nitrogen atom and (ii) a homopolymer of an unsaturated acid; and (III) preserving the slurry against bacterial contamination, while avoiding instantaneous heterogeneous thickening of the slurry due to the tetrakis(hydroxyorgano)phosphonium salt.

16 Claims, No Drawings

METHODS FOR TREATING AN INORGANIC SLURRY

CROSS-REFERENCE TO RELATED APPLICATIONS

This application is a continuation application of application Ser. No. 13/586,012 filed Aug. 15, 2012 (abandoned), which is a continuation application of application Ser. No. 10/542,432 filed Nov. 16, 2005 (abandoned), which is a United States national phase application of International application PCT/GB 2004/000056 filed Jan. 12, 2004. The entire contents of each of Ser. Nos. 13/586,012 and 10/542,432 and International application PCT/GB 2004/000056 are hereby incorporated by reference herein.

This invention relates to a composition for treating inorganic slurries and to a method of treating inorganic slurries with the aforesaid composition so as to maintain the slurries in a substantially homogeneous phase.

The present invention will be described herein with particular reference to calcium carbonate-based slurries, especially those used in paper-making processes, although it is not to be construed as being limited thereto.

Most inorganic slurries contain about 70% to 80% by weight of solids. Many inorganic slurries (particularly those based on calcium carbonate) are known to be susceptible to bacterial contamination and it has been the practice to add one or more biocidally-active materials to the slurries in order to minimise such contamination.

Phosphorus-containing compounds, in particular tetrakis (hydroxyorgano)phosphonium salts ($THP^+$ salts) are known to be effective biocides. Experimental work carried out by the applicants has shown, for example, that the addition of a solution of tetrakis(hydroxymethyl)phosphonium sulphate (THPS) to a calcium carbonate-based slurry can give rise to a reduction in bacterial count of $10^4$ in 2 hours.

However, it is also known that addition of THPS alone to a slurry results in instantaneous heterogeneous thickening and aggregation of the slurry.

The applicants have found that the use of a composition comprising a $THP^+$ salt and a dispersant will provide continuing preservation against bacterial contamination, while at the same time maintaining the slurry in a substantially homogeneous phase.

Accordingly, in a first aspect, the present invention provides a composition for treating an inorganic slurry, the composition comprising:

(a) a tetrakis(hydroxyorgano)phosphonium salt (hereinafter $THP^+$ salt); and
(b) a dispersant selected from the group consisting of:
  (i) phosphonated compounds containing at least one tertiary nitrogen atom;
  (ii) phosphonated oligomers of unsaturated acids;
  (iii) homopolymers of unsaturated acids;
  and (iv) polyphosphates.

In accordance with the present invention, the $THP^+$ salt is preferably tetrakis(hydroxymethyl)phosphonium sulphate.

Alternatively, the $THP^+$ salt may be tetrakis(hydroxymethyl)phosphonium chloride, phosphate, nitrate or oxalate.

A preferred example of a dispersant of the type (b)(i) is a compound having one tertiary nitrogen atom, such as a sodium salt of nitrilotris(methylene phosphate), particularly the tetra-sodium salt.

Preferred examples of dispersants of the type (b)(ii) include those oligomers having the general $H(CH_2OM.CH_2OM)_nPO_3M_2$, wherein M is a cationic species such that the oligomer is soluble in water and n is a number greater than 1.

Other suitable oligomers are disclosed in the applicant's European Patent Specification 0 491 391.

A preferred example of a dispersant of the type (b)(iii) is a homopolymer of acrylic acid, especially a homopolymer having a molecular weight in the range 2000 to 5000.

Preferred examples of dispersants of the type b(iv) include sodium tripolyphosphate.

In a second aspect, the present invention provides a method of treating an inorganic slurry to maintain the slurry in a substantially homogeneous phase, the method comprising the addition to the slurry of an effective amount of a composition according to the first aspect of the present invention.

The inorganic slurry may, for example, comprise a calcium carbonate-based slurry.

Alternatively, the inorganic slurry may comprise a pigment slurry, a clay slurry or a cement slurry.

Preferably, the ratio of $THP^+$ salt to dispersant in the composition is about 2:1 (as active ingredients).

Suitably, the composition may be added to the slurry in an amount in the range 10 ppm to 1000 ppm (by weight of the slurry), for example about 750 ppm (by weight of the slurry).

The present invention will be illustrated by way of the following examples.

In the examples, a 75% calcium carbonate slurry (commercially known as Setacarb) was treated with:

EXAMPLE 1

$THP^+$ salt alone.

EXAMPLE 2

$THP^+$ salt and dispersant of type (b)(i).

EXAMPLE 3

$THP^+$ salt and dispersant of type (b)(ii).

The amounts of each additive used, and the results, are given in the TABLE below.

TABLE

| Example No. | $THP^+$ salt (ppm) | Dispersant (ppm) | Result |
|---|---|---|---|
| 1 | (a) THPS 750 ppm | (b) (nil) | Instant heterogeneous thickening |
| 2 | (a) THPS 750 ppm | b (i) 375 ppm | No thickening |
| 3 | (a) THPS 750 ppm | b (ii) 375 ppm | No thickening |

Notes to TABLE
(a) An aqueous solution of tetrakis(hydroxymethyl)phosphonium sulphate (75% a.i.), available as TOLCIDE ®-PS75.
(b) (i) An aqueous solution of the tetra sodium salt of nitrilotris (methylene phosphonic acid), available as BRIQUEST ® 301-32S.
(b) (ii) A homopolymer of polyacrylic acid, having a molecular weight in the range 2000-5000 and available as BEVALOID ® 211.

The invention claimed is:
1. A method for treating an inorganic slurry to preserve the slurry against bacterial contamination, comprising the steps of:
(I) providing a slurry in a substantially homogeneous phase, and then
(II) adding to said slurry an effective amount of a composition comprising:

(a) a tetrakis(hydroxyorgano)phosphonium salt selected from the group consisting of
tetrakis(hydroxymethyl)phosphonium sulphate, tetrakis(hydroxymethyl)phosphonium chloride, tetrakis(hydroxymethyl)phosphonium phosphate, tetrakis(hydroxymethyl)phosphonium nitrate and tetrakis(hydroxymethyl)phosphonium oxalate; and
(b) a dispersant selected from the group consisting of
(b)(i) a sodium salt of nitrilo-tris(methylene phosphonate) and
(b)(ii) a homopolymer of acrylic acid having a molecular weight in the range of 2,000 to 5,000; and
(III) preserving the slurry against bacterial contamination, whilst avoiding instantaneous heterogeneous thickening of the slurry due to the tetrakis(hydroxyorgano)phosphonium salt.

2. The method according to claim 1, wherein the tetrakis(hydroxyorgano)phosphonium salt is tetrakis(hydroxymethyl)phosphonium sulphate.

3. The method according to claim 1 wherein the tetrakis(hydroxyorgano)phosphonium salt is tetrakis(hydroxymethyl)phosphonium chloride, tetrakis(hydroxymethyl)phosphonium phosphate, tetrakis(hydroxymethyl)phosphonium nitrate or tetrakis(hydroxymethyl)phosphonium oxalate.

4. The method according to claim 1, wherein the dispersant is a sodium salt of nitrilo-tris(methylene phosphonate).

5. The method according to claim 4, wherein the salt is the tetra-sodium salt.

6. The method according to claim 1, wherein the dispersant is a homopolymer of acrylic acid having a molecular weight in the range of 2,000 to 5,000.

7. The method according to claim 1, wherein the ratio of tetrakis(hydroxyorgano)phosphonium salt to dispersant in the composition is about 2:1, as active ingredients.

8. The method according to claim 1, wherein the composition is added to said slurry in an amount in the range of 10 ppm to 1000 ppm, by weight of said slurry.

9. The method according to claim 1, wherein the composition is added to said slurry in an amount of about 750 ppm, by weight of said slurry.

10. The method according to claim 1, wherein said slurry comprises a calcium carbonate-based slurry.

11. The method according to claim 1, wherein said slurry comprises a pigment slurry, a clay slurry or a cement slurry.

12. The method of claim 1, wherein said slurry contains 70 to 80% by weight of undissolved suspended solids.

13. The method of claim 1, wherein said slurry comprises a calcium carbonate slurry that contains 70 to 80% or more, by weight, of undissolved suspended solids.

14. The method of claim 13, wherein the composition is added to said slurry in an amount in the range of 10 ppm to 1000 ppm, by weight of said slurry.

15. A method for treating an inorganic slurry to preserve the slurry against bacterial contamination, comprising the steps of:
(I) providing a slurry in a substantially homogeneous phase, and then
(II) adding to the slurry an effective amount of a composition comprising:
(a) a tetrakis(hydroxyorgano)phosphonium salt selected from the group consisting of tetrakis(hydroxymethyl)phosphonium sulphate, tetrakis(hydroxymethyl)phosphonium chloride, tetrakis(hydroxymethyl)phosphonium phosphate, tetrakis(hydroxymethyl)phosphonium nitrate and tetrakis(hydroxymethyl)phosphonium oxalate; and
(b) a dispersant which is the tetra sodium salt of nitrilo-tris(methylene phosphonate); and
(III) preserving the slurry against bacterial contamination, whilst avoiding instantaneous heterogeneous thickening of the slurry due to the tetrakis(hydroxyorgano)phosphonium salt.

16. A method for treating an inorganic slurry to preserve the slurry against bacterial contamination, comprising the steps of:
(I) providing a slurry in a substantially homogeneous phase, and then
(II) adding to the slurry an effective amount of a composition comprising:
(a) a tetrakis(hydroxyorgano)phosphonium salt selected from the group consisting of tetrakis(hydroxymethyl)phosphonium sulphate, tetrakis(hydroxymethyl)phosphonium chloride, tetrakis(hydroxymethyl)phosphonium phosphate, tetrakis(hydroxymethyl)phosphonium nitrate and tetrakis(hydroxymethyl)phosphonium oxalate; and
(b) a dispersant which is a homopolymer of acrylic acid, the homopolymer having a molecular weight in the range of 2,000 to 5,000, and
(III) preserving the slurry against bacterial contamination, whilst avoiding instantaneous heterogeneous thickening of the slurry due to the tetrakis(hydroxyorgano)phosphonium salt.

* * * * *